United States Patent [19]

McCarthy

[11] Patent Number: 5,514,138
[45] Date of Patent: May 7, 1996

[54] CONNECTOR HAVING A STOP MEMBER

[75] Inventor: Thomas F. McCarthy, Neshanic Station, N.J.

[73] Assignee: Pfizer Inc., New York, N.Y.

[21] Appl. No.: 191,974

[22] Filed: Feb. 4, 1994

Related U.S. Application Data

[63] Continuation of Ser. No. 925,302, Aug. 5, 1992, abandoned, which is a continuation of Ser. No. 652,701, Feb. 8, 1991, abandoned.

[51] Int. Cl.[6] .......................... A61B 17/58; A61B 17/56
[52] U.S. Cl. .................. 606/65; 606/66; 606/69
[58] Field of Search ................ 606/53, 60, 65–71

[56] References Cited

U.S. PATENT DOCUMENTS

| | | | |
|---|---|---|---|
| 2,243,717 | 5/1941 | Moreira | 606/65 |
| 2,702,543 | 2/1955 | Pugh et al. | 606/65 X |
| 3,374,786 | 3/1968 | Callender et al. | 606/60 |
| 4,379,451 | 4/1983 | Getscher | 606/68 |
| 4,612,920 | 9/1986 | Lower | 606/66 |
| 4,628,923 | 12/1986 | Medoff | 606/65 |
| 4,657,001 | 4/1987 | Fixel | 606/66 |
| 4,934,861 | 6/1990 | Weeks et al. | 403/408.1 |
| 4,964,403 | 10/1990 | Karás et al. | 606/60 |

Primary Examiner—Robert A. Hafer
Assistant Examiner—Brian E. Hanlon
Attorney, Agent, or Firm—Peter C. Richardson; Gezina Holtrust; B. Timothy Creagan

[57] ABSTRACT

An improved device for repairing fractured bones is provided, the device comprising a specially designed connector, which is especially useful in combination with a plate having a tab cut out, a stop, a flat portion and a bore portion and with a compression screw and a lag screw.

4 Claims, 3 Drawing Sheets

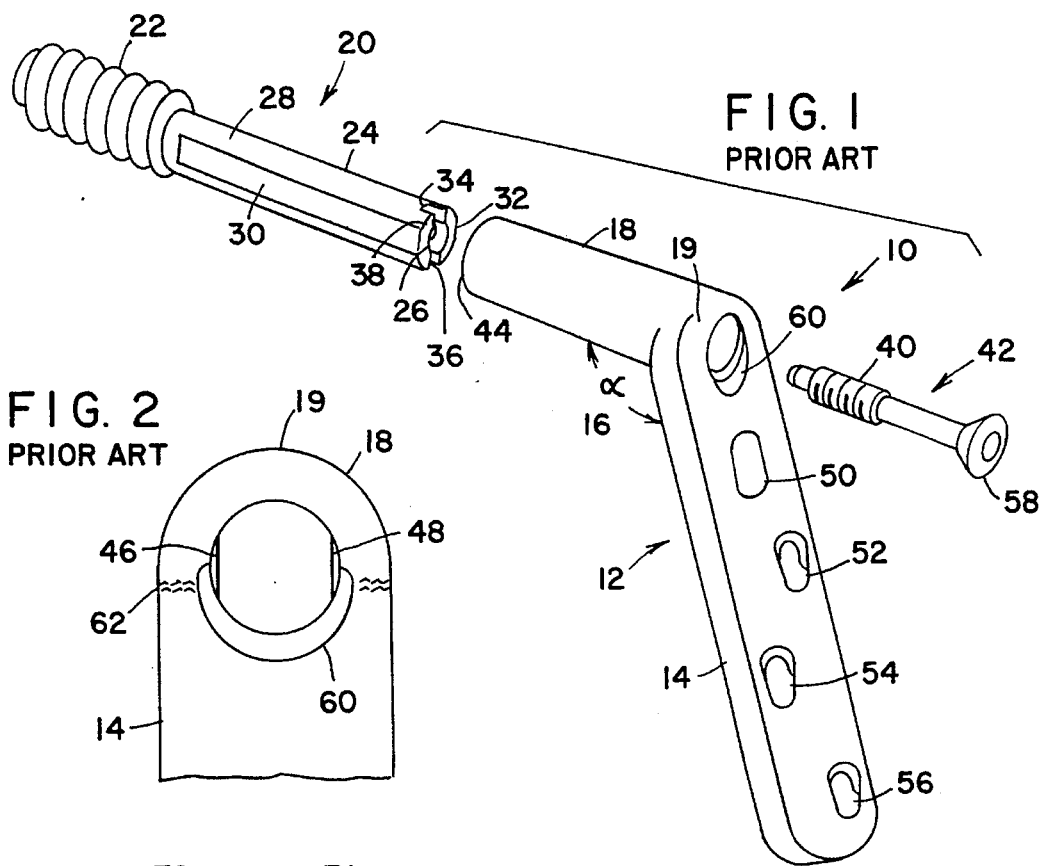
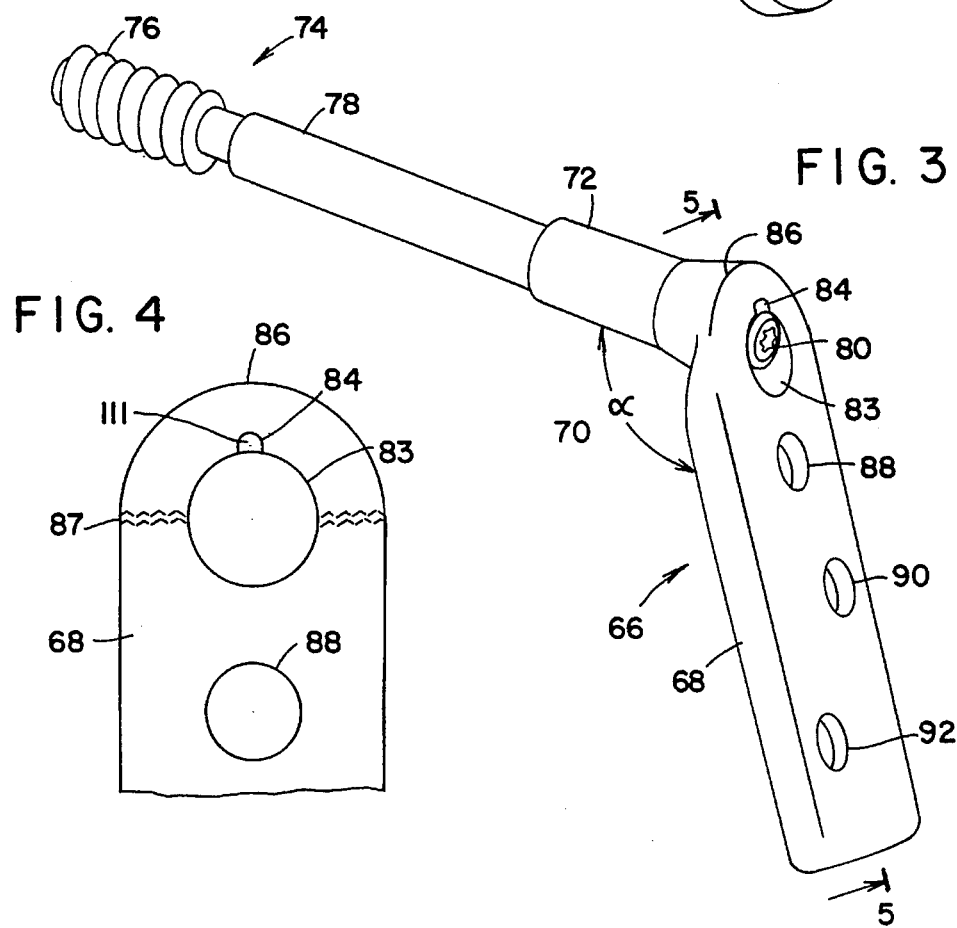

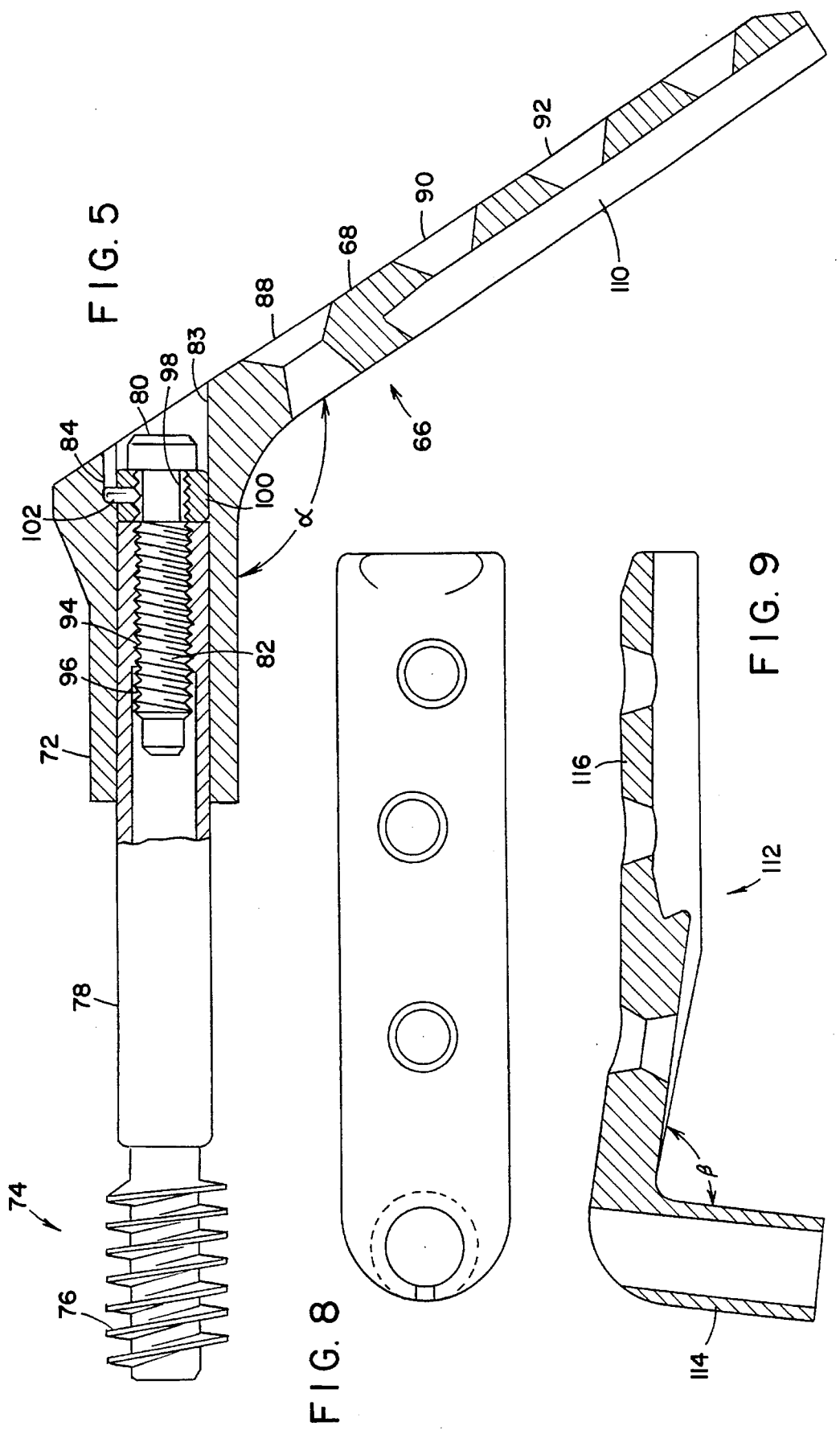

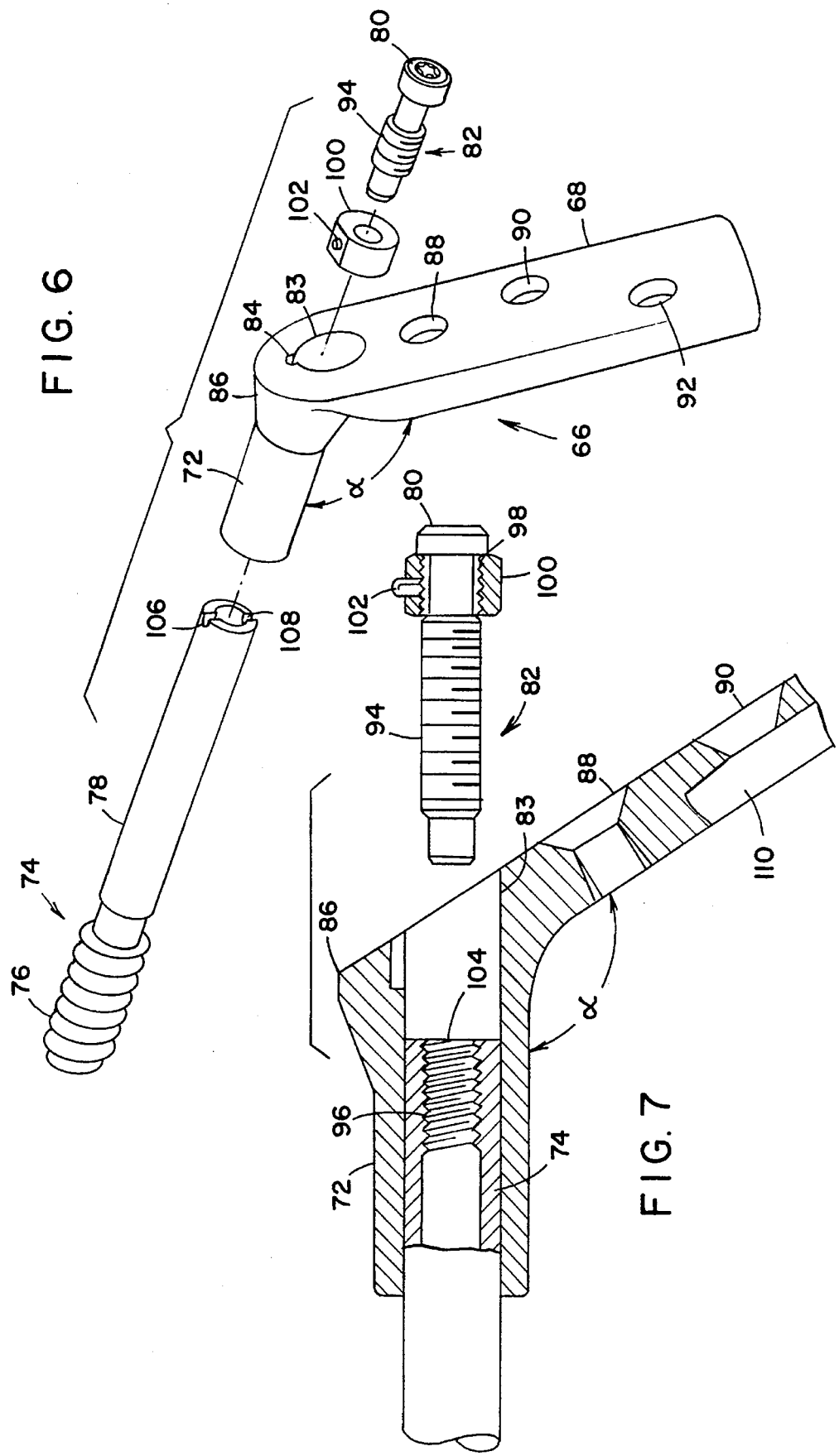

CONNECTOR HAVING A STOP MEMBER

This is a continuation, of application Ser. No. 07/925,302, filed on Aug. 5, 1992, now abandoned which was a continuation of application Ser. No. 07/652,701 filed on Feb. 8, 1991, now abandoned.

BACKGROUND OF THE INVENTION

This invention relates to connectors and relates in particular to connectors which connect lag screws and bone plates.

In the prior art, in order to repair a fractured bone (for example a proximal femur or a distal femur) generally a combination of a lag screw with a side plate or a combination of a lag screw with a supracondylar plate has been used. Also, a compression screw is used if compression or reduction of the fracture is desired. In such prior art devices, the plates which have been used have a flat portion with holes therein for bone screws. Each plate also has a portion generally in the form of and positioned at an angle with respect to the flat portion. Through the barrel portion, a compression screw can be threaded, if desired. Generally, this compression screw is supported by the plate but within a cutout therein. However, in these prior art plates, when the flat portion of the side plate or of the supracondylar plate is stressed to a sufficient degree, the plates sometimes break near the intersection of the compression screw with the plate.

An object of this invention is an improved device for repairing bone fractures which is significantly stronger than prior art devices.

SUMMARY OF THE INVENTION

This and other objects are satisfied by the device of the invention which comprises a connector (also called a compression screw insert herein) having a tab for use with a compression screw, the tab allowing the compression screw to fit into and be secured within the barrel portion of a cannulated lag screw which fits into the barrel portion of a side plate or supracondylar plate, such that the head of the compression screw lies relatively flat with respect to the plate when the compression screw is inserted into the lag screw.

Also according to the invention, a compression screw insert comprises a threaded washer having (a) a thread located on the inner circumference of the washer and (b) a tab (or alternatively a tab cutout) located on the outer circumference of the washer (the tab or tab cutout to be fitted either into a tab cutout or tab respectively located on another element).

Also according to the invention, a compression screw insert assembly comprises (a) the compression screw insert described above, (b) a plate having a flat portion and a bore portion integral with and angled with respect to each other (within which either the tab or the tab cutout is located) and (c) a compression screw.

Also according to the invention in another embodiment the compression screw insert assembly described above includes also a lag screw.

BRIEF DESCRIPTION OF THE DRAWINGS

FIG. 1 is an exploded view of a pictorial representation of a prior art device for use in repairing fractures of a proximal portion of a femur, showing a cannulated lag screw with a barrel portion that fits within a barrel portion of a side plate, the barrel portion of the side plate being integral with and angled with respect to the relatively flat plate portion of the side plate into which a threaded compression screw is inserted. The head of the compression screw is stopped by and is supported within a cutout in the side plate, such that when the compression screw is threaded into the thread of the lag screw, the uppermost extremity of the head of the compression screw lies substantially flush with the upper surface of the flat plate portion (when the device is first inserted into a patient, although the device permits later possible pistoning).

FIG. 2 is a pictorial representation of a view of the prior art side plate of FIG. 1, sighting along and into the barrel portion of the side plate and showing the cutout in the prior art device into which the compression screw is seated when the compression screw is fully inserted within the side plate. Lines of potential fracture are indicated.

FIG. 3 is a pictorial view of an embodiment of the device of the invention showing a compression screw assembly seated within the side plate such that the tab of the compression screw insert fits within the tab cutout in the barrel portion of the side plate.

FIG. 4 is a pictorial view of a portion of the side plate of FIG. 3 as viewed into the barrel portion of the side plate, showing the tab cutout located within the barrel portion of the side plate and at the intersection of the flat portion of the side plate with the barrel portion of the side plate. Lines of potential fracture are indicated.

FIG. 5 is a view in cross-section of the device shown in FIG. 3 taken along the lines 5—5 in FIG. 3.

FIG. 6 is an exploded pictorial representation of the device shown in FIG. 3 showing a cannulated lag screw with a hollow internally threaded barrel portion (threading shown in FIG. 5 but not in FIG. 6) and with a smooth exterior surface, a side plate having a barrel portion angled with respect to a substantially flat plate portion, and a connector insert having a tab portion thereon (which fits within a tab cutout in the barrel portion of the device) and the connector insert being internally threaded so that it mates with the threading of the compression screw.

FIG. 7 is a partial view in cross-section of the device of FIG. 3, but with the compression screw insert threaded onto the compression screw and with the barrel portion of the lag screw inserted into the barrel portion of the side plate.

FIG. 8 is a pictorial elevational view of a supracondylar plate for use with the compression screw insert, lag screw and compression screw, described above for FIGS. 3–7, showing the barrel portion of that plate angled with respect to the substantially flat portion of that plate at an angle B (wherein B is smaller than angle α described above and shown in FIG. 3).

FIG. 9 is a view in cross-section of the supracondylar plate shown in FIG. 8.

DESCRIPTION OF THE PREFERRED EMBODIMENTS

In FIG. 1, a prior art device for use in repairing fractures of a proximal femur is shown. A side plate 12 has a substantially flat plate portion 14 and a barrel portion 18, which are integrally connected together at an angle α 16. A cannulated lag screw 20 has a threaded portion 22 at one end thereof and a rod portion 24, the two portions being integral. Lag screw 20 has a cannulated interior 26, the cross-section of which is circular. The rod portion 24 has an exterior surface, a portion 28 of which is round and a portion of which is bounded by two substantially parallel substantially flat surfaces 30, 32.

Rod portion 24 has two cutouts 34, 36 at the free end 38 of rod portion 24 (i.e., at the end of rod portion 24 not connected to threaded portion 22). Located within rod portion 24 near free end 38 is an internal threading (not shown) into which the threading 40 of compression screw 42 mates. Barrel portion 18 of side plate 12 has located internally therein at end 44 two substantially flat portions 46, 48 (shown in FIG. 2 but not in FIG. 1), into which substantially parallel flat surfaces 30, 32 fit and are locked therebetween so as to prevent rod portion 24 from rotating within barrel portion 18. Rod portion 24 is slightly longer than barrel portion 18 and is free to piston therein.

Substantially flat plate portion 14 has a multiplicity of holes 50, 52, 54, 56 located therein, into which bone screws (not shown) can be inserted. Compression screw 42 has a head 58, such that when threading 40 is threaded into the threading within rod portion 24 (not shown), head 58 can be seated within cutout 60 in barrel portion 18. Cutout 60 is a space cut out from the material of substantially flat plate portion 14 of side plate 12. When side plate 12 is sufficiently stressed, such prior art plates having such a cutout design have been found to fail and break, at positions represented by the dotted lines 62 in FIG. 2.

In FIG. 3, an embodiment of the device of the invention for use in repairing fractures of a proximal femur is shown. A side plate 66 has a substantially flat plate portion 68 and a barrel portion 72, which parts are integral with each other and positioned at an angle α 70 with respect to each other. Lag screw 74 is shown with its threaded portion 76 to be threaded into bone and its rod portion 78 inserted within barrel portion 72 of side plate 66. Head 80 of compression screw 82 (see FIG. 5) is located within barrel portion 72 of side plate 66. A tab cutout 84 having a stop face 111 within barrel portion 72 is located at the position closest to the proximal end 86 of the substantially flat plate portion 68 of side plate 66. Also shown are holes 88, 90, and 92 in substantially flat plate portion 68. Circular barrel portion 83 is located within substantially flat plate portion 68.

As shown in FIG. 4, tab cutout 84 is located within substantially flat plate portion 68 as near as possible to proximal end 86 thereof. Lines of potential fracture 87 are indicated.

In FIG. 5, the device of FIG. 3 is shown in its assembled position in cross-section. Lag screw 74 (to be placed within bone) has a threaded portion 76 at one end thereof and a barrel portion 78 at the other end thereof. Barrel portion 78 fits within barrel portion 72 of side plate 66 and is free to rotate and piston therein. Compression screw 82 has threading 94 which mates with internal threading 96 of lag screw 74. Threading 94 of compression screw 82 additionally mates with internal threading 98 of compression screw insert 100 located on its inner circumference. Compression screw insert 100 has a tab portion 102 located on its outer circumference. Tab portion 102 fits within tab cutout 84 in circular barrel portion 83 of substantially flat plate portion 68, thereby permitting compression screw 82 to be positioned within flat plate portion 68 so that its head 80 lies substantially flush with the surface of flat plate portion 68.

Shown in FIG. 6 is a pictorial exploded view of the device of FIG. 3, with similar parts numbered similarly. Compression screw insert 100 with tab portion 102 is shown separated from compression screw 82. Also shown is free end 104 (see FIG. 7) of lag screw 74, which has two cutouts 106, 108. These two cutouts are used with an insertion device for inserting lag screw 74 into bone and are not related to the functioning of tab portion 102.

In FIG. 7 lag screw 74 is shown at a time when free end 104 thereof is positioned within circular barrel portion 83, but when compression screw 82 is not yet inserted into circular barrel portion 83 and threaded together with internal threading 96 of lag screw 74. Also shown in FIGS. 5 and 7 are cutaway portions 110 in substantially flat plate portion 68.

Shown in FIG. 9 is a cross-sectional view of a supracondylar plate 112 which can be used instead of side plate 66 (described above and shown in FIGS. 3–7) in an alternative embodiment of the device of the invention. Supracondylar plate 112 is similar to side plate 66, but the barrel portion 114 thereof is positioned at an angle β (instead of angle α) with respect to the substantially flat plate portion 114 of supracondylar plate 112.

Angle α generally will lie within the range from about 130° to about 150°.

Angle β will be about 95°.

Alteratively, if desired, any other suitable plate can be substituted for side plate 66 for use with the connector insert 100 described above.

To use the device of the invention, a suitable method is the following. (1) Lag screw 74 is first inserted into a bone having a fracture therein by means of an insertion tool (not shown) which interacts with two cutouts 106,108 at free end 104 of lag screw 74. (2) Next either side plate 66 or supracondylar plate 112 (or other suitable plate) is positioned so that either barrel 72 of side plate 66 or barrel 114 of supracondylar plate 112, respectively, is placed onto barrel 78 of lag screw 74. (3) Insert the connector 100 into the barrel portion 72 of the plate 66 (or 112) so that the tab 102 fits as far as possible into the tab cutout 84. (4) Using a screwdriver placed into the compression screw head 80, insert the compression screw 82 into and through the connector 100 until the compression screw 82 meets the lag screw 74. The compression screw 82 will advance into the lag screw 74 until the head 80 of the compression screw 94 rests against the connector 100. If the compression screw 82 is further turned, it will draw the lag screw 74 into the barrel portion 72 of the plate (66 or 112) thereby reducing the fracture. This turning of the compression screw 82 is continued until the surgeon determines that the fracture is sufficiently reduced.

It has been found that when the compression screw insert 100 (as herein described) is used with the compression screw 82, with the side plate 66 (or supracondylar plate 112) having the tab cutout 84 (as herein described), and with the lag screw 74, the side plate 66 (and the supracondylar plate 112) can withstand substantially greater stresses before they fail than prior art devices having cutout 60.

I claim:

1. A device for lagging two bone segments comprising:

a lag screw having a first end for engaging one of said bone segments and a second end having a threaded bore;

a bone plate for engaging the other of said bone segments and having a bore formed therein having first and second ends for slidably receiving said lag screw, said bore having a tab cutout formed on said bore said tab cutout having a stop face intermediate said ends;

a threaded element insertable within said bore plate from one end of the bore for engaging the threaded bore of said lag screw, said threaded element having a free end and a compression screw insert having an inward face, an outward face and a radially extending tab portion, said tab portion having an axially inwardly facing stop surface for engaging the stop face of said tab cutout of said bone plate, said radially extending tab portion engaging said stop face of the tab cutout of said bone plate when said tab portion is fully advanced along said tab cutout, said stop face of the tab cutout of said bone plate having a length such that upon engagement of said radially extending tab portion with said stop face of said tab cutout and the engagement of said outward face of said compression screw insert with the free end of said threaded element, the inward face of said compression screw insert is spaced from said second end of said lag screw to permit longitudinal outward movement from said stop face of said tab cutout of said lag screw upon rotation of said threaded element.

2. A device for lagging two bone segments according to claim 1 wherein said plate further comprises a substantially flat plate portion, said bore being integral with and angled with respect to said flat plate portion.

3. A device for lagging two bone segments according to claim 1, wherein said compression screw insert has a threaded internal bore which mates with the threads on said threaded element.

4. A device for lagging two bone segments according to claim 1, wherein said bone plate is a supracondylar plate.

\* \* \* \* \*